US00PP16026P2

(12) United States Plant Patent
Stade

(10) Patent No.: US PP16,026 P2
(45) Date of Patent: Oct. 4, 2005

(54) ***LIGULARIA* PLANT NAMED 'LATERNCHEN'**

(50) Latin Name: *Ligularia×Hessei*
Varietal Denomination: Laternchen

(75) Inventor: Helmut Stade, Borken-Marbech (DE)

(73) Assignee: Witteman & Company, Hillegom (NL)

( * ) Notice: Subject to any disclaimer, the term of this patent is extended or adjusted under 35 U.S.C. 154(b) by 0 days.

(21) Appl. No.: 10/949,951

(22) Filed: Sep. 24, 2004

(51) Int. Cl.[7] ..... A01H 5/00
(52) U.S. Cl. ..... Plt./263
(58) Field of Search ..... Plt./263

*Primary Examiner*—Anne Marie Grunberg
(74) *Attorney, Agent, or Firm*—C. A. Whealy

(57) ABSTRACT

A new and distinct cultivar of *Ligularia* plant named 'Laternchen', characterized by its relatively compact and short plant habit; freely flowering habit; golden yellow ray and disc florets; and good garden performance.

3 Drawing Sheets

Botanical classification/cultivar designation: *Ligularia×Hessei* cultivar Laternchen.

BACKGROUND OF THE INVENTION

The present Invention relates to a new and distinct cultivar of *Ligularia* plant, botanically known as *Ligularia×Hessei*, and hereinafter referred to by the cultivar name Laternchen.

The new *Ligularia* is a naturally-occurring whole plant mutation of the *Ligularia×Hessei* cultivar Gregynog Gold, not patented. The new *Ligularia* was discovered and selected by the Inventor as a single plant within a population of plants of the cultivar Gregynog Gold in a controlled environment in Borken-Marbech, Germany, in 1996.

A sexual reproduction of the new cultivar by divisions at Borken-Marbech, Germany since 1996, has shown that the unique features of this new *Ligularia* are stable and reproduced true to type in successive generations.

SUMMARY OF THE INVENTION

Plants of the cultivar Laternchen have not been observed under all possible environmental conditions. The phenotype may vary somewhat with variations in environment such as temperature and light level without, however, any variance in genotype.

The following traits have been repeatedly observed and are determined to be the unique characteristics of 'Laternchen'. These characteristics in combination distinguish 'Lanternchen' as a new and distinct cultivar of *Ligularia:*

1. Relatively compact and short plant habit.
2. Freely flowering habit.
3. Golden yellow ray and disc florets.
4. Good garden performance.

Plants of the new *Ligularia* are most similar to plants of the parent, the cultivar Gregynog. Compared to plants of the cultivar Gregynog Gold and other cultivars of *Ligularia* known to the Inventor, plants of the new *Ligularia* are more compact, shorter and differ in inflorescence shape.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which more accurately describe the actual colors of the new *Ligularia.*

The photograph on the first sheet comprises a side perspective view of a typical flowering plant of 'Laternchen'.

The photograph at the top of the second sheet comprises a side perspective view of a typical vegetative plant of 'Laternchen'.

The photograph at the bottom of the second sheet is a close-up view of a typical vegetative plant of 'Laternchen'.

The photograph at the top of the third sheet is a close-up view of a typical inflorescence of 'Laternchen'.

The photograph at the bottom of the third sheet is a close-up view of a typical leaf of 'Laternchen'.

DETAILED BOTANICAL DESCRIPTION

The aforementioned photographs, following observations and measurements describe plants grown in Lisse, The Netherlands, in an outdoor nursery and under commercial production practices during the summer. Plants were grown in 17-cm containers and were about one year old when the photographs and description were taken. During the production of the plants, day temperatures ranged from 14 to 31° C. and night temperatures ranged from 4 to 16° C. In the following description, color references are made to The Royal Horticultural Society Colour Chart, 2001 Edition, except where general terms of ordinary dictionary significance are used.

Botanical classification: *Ligularia×Hessei* cultivar Laternchen.

Parentage: Naturally-occurring whole plant mutation of the *Ligularia×Hessei* cultivar Gregynog Gold, not patented.

Propagation:

*Type.*—By divisions.

*Time to initiate roots, winter.*—About 15 days at 14° C.

*Time to produce a rooted plant, winter.*—About 40 days at 20° C.

*Root description.*—Thick, fleshy.

Plant description:

*Plant form/habit.*—Perennial flowering plant. Compact and upright plant habit; narrowly inverted triangle; moderately vigorous growth habit. Single inflorescence form; basal leaves in a rosette.

*Plant height.*—About 67 cm.

*Plant width* (*spread*).—About 33.7 cm.

*Number of flowering stems per plant.*—About three.

*Flowering stem description.*—Length: About 46 cm. Diameter: About 5 mm. Internode length: About 14.8 cm. Aspect: Erect. Strength: Strong. Texture: Sparsely pubescent. Color: N186C. Lenticels: Length: About 2 mm. Width: About 0.3 mm. Color: 143A.

*Foliage description.*—Arrangement: Basal leaves; rosette; flowering stem leaves, alternate; simple. Quantity: Basal leaves: About 20 per plant. Flowering stem leaves: About three per stem. Leaf length: About 12.3 cm. Leaf width: About 14.2 cm. Shape: Roughly triangular to reniform. Apex: Acute. Base: Hastate to reniform. Margin: Serrate. Texture, upper and lower surfaces: Smooth, glabrous. Venation pattern: Reticulate. Color: Developing leaves, upper surface: 144A. Developing leaves, lower surface: 146B. Fully expanded leaves, upper surface: Between 137A and 146A; margins, close to 59A. Fully expanded leaves, lower surface: 137C. Venation, upper surface: 176A to 176B. Venation, lower surface: 177C to 177D. Petiole: Length: Basal leaves: About 24.4 cm. Flowering stem leaves: About 13.2 cm. Diameter: About 4 mm. Texture, upper and lower surfaces: Sparsely pubescent. Color, upper and lower surfaces: 177A; longitudinal stripes, 143B.

Inflorescence description:

*Appearance.*—Single inflorescence form with linear to narrowly oblong-shaped ray florets. Inflorescences terminal and axillary. Disk and ray florets develop acropetally on a capitulum. Inflorescences slightly fragrant. Inflorescences face upright to slightly outwardly. Inflorescences persistent.

*Flowering response.*—In The Netherlands, plants flower continuously from June to early August.

*Inflorescence longevity.*—Inflorescences maintain good color and substance of about four weeks on the plant.

*Quantity of inflorescences.*—About 22 inflorescences and inflorescence buds per flowering stem.

*Inflrescence bud.*—Height: About 1.6 cm. Diameter: About 5 mm. Shape: Ovoid. Color: 144B; towards the apex, 13A.

*Inflorescence diameter.*—About 12.7 cm.

*Inflorescence height.*—About 2.1 cm.

*Diameter of disc.*—About 1.2 cm.

*Receptacle diameter.*—About 7 mm.

*Receptacle height.*—About 1.4 cm.

*Ray florets.*—Shape: Linear to narrowly oblong. Aspect: Reflexed; somewhat twisted. Length: About 2.5 cm. Width: About 7 mm. Apex: Retuse to emarginate. Base: Obtuse. Margin: Entire: Texture: Smooth, glabrous. Number of ray florets per inflorescence: About seven in a single whorl. Color: When opening, upper surface: Close to 12A to 9A. When opening, lower surface: Close to 12A to 12B. Fully opened, upper surface: Close to 9A to 12A. Fully opened, lower surface: Close to 12A.

*Disc florets.*—Arrangement: Massed at center of receptacle. Shape: Tubular, salverform. Apex: Five-pointed. Length: About 1.1 cm. Diameter, apex: About 4 mm. Diameter, base: About 2 mm. Number of disc florets per inflorescence: About 14. Color: Immature: 153A to 153B. Apex: 9A to 9B. Midsection: 2B. Base: 1A to 2B.

*Phyllaries.*—Quantity per inflorescence: About eight in a single whorl. Length: About 1.5 cm. Width: About 1.8 mm. Shape: Linear. Apex: Acute. Base: Cuneate. Margin: Entire. Texture, upper and lower surfaces: Smooth; glabrous. Color, upper and lower surfaces: 144B.

*Peduncles.*—Length: Terminal peduncle: About 1.2 cm. Fourth peduncle: About 9 mm. Diameter: About 2 mm. Angle to vertical: About 20° from vertical. Strength: Moderately strong, flexible. Texture: Smooth, glabrous. Color: 177A; longitudinal stripes, 143B.

*Reproductive organs.*—Androecium: Stamens per floret: About two. Filament color: N199B. Anther shape: Linear. Anther length: About 2 mm. Anther color: 17B. Pollen amount: Scarce. Pollen color: 17B. Gynoecium: Pistil length: About 5 mm. Style length: About 3 mm. Style color: 17D. Stigma color: 17C. Ovary color: 144C. Pappus: Appearance: Hairlike; fine. Length: About 6 mm. Diameter: Less than 1 mm. Color: 199C.

*Seed/fruit.*—Seed and fruit production has not been observed.

Disease/pest resistance: Resistance to pathogens and pests common to *Ligularias* has not been observed on plants grown under commercial greenhouse or outdoor nursery conditions.

Garden performance: Plants of the new *Ligularia* have been observed to be rain and wind tolerant and to tolerate USDA Hardiness Zone 5 and high temperatures to at least 35° C.

It is claimed:

1. A new and distinct cultivar of *Ligularia* plant named 'Laternchen', as illustrated and described.

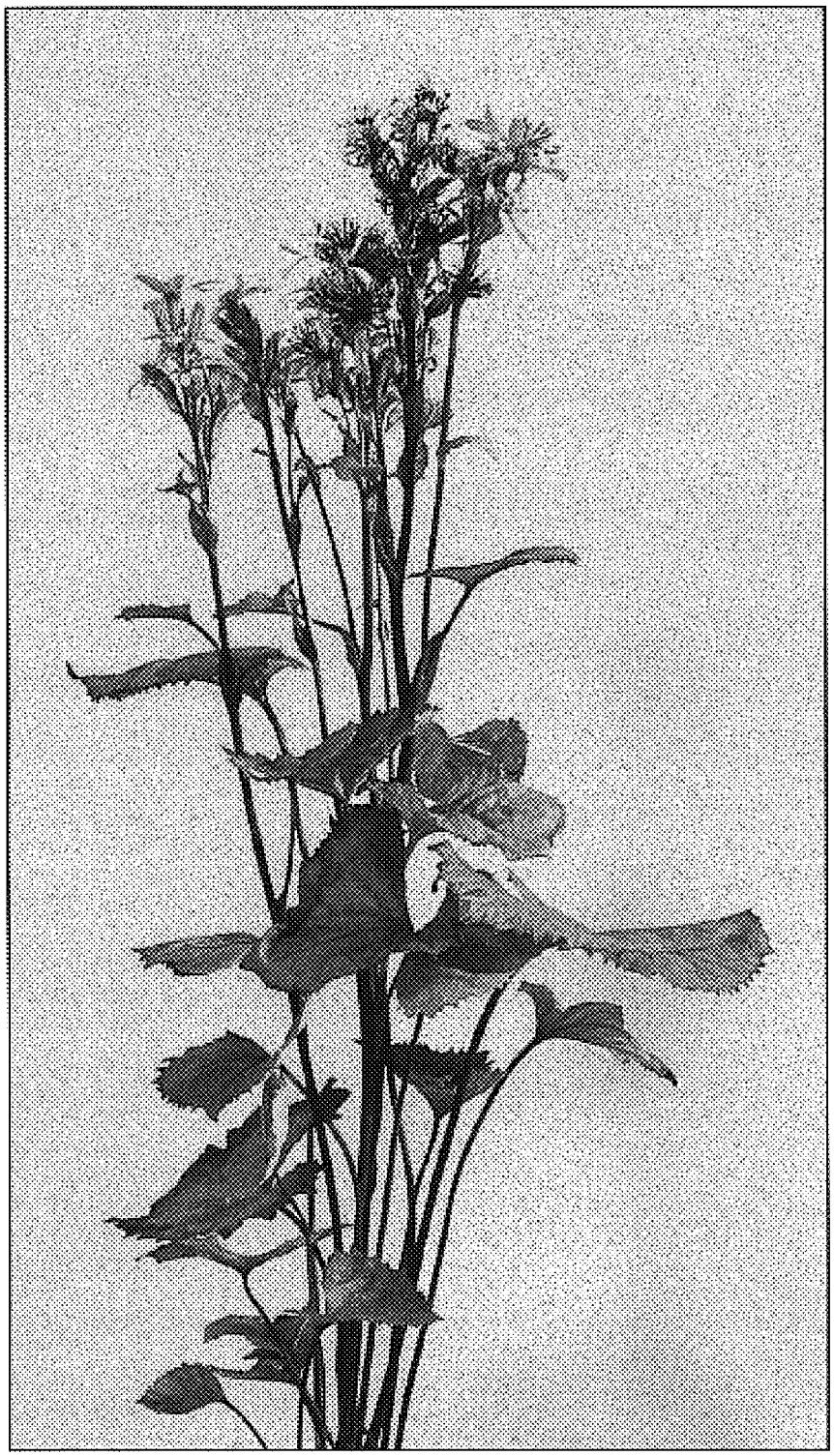

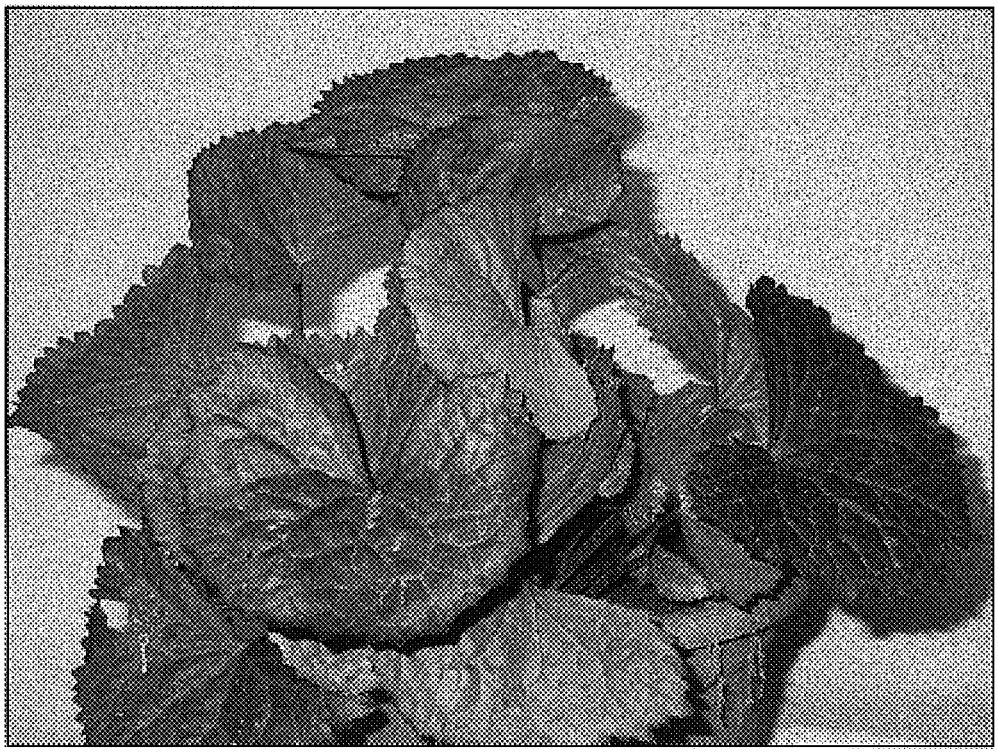
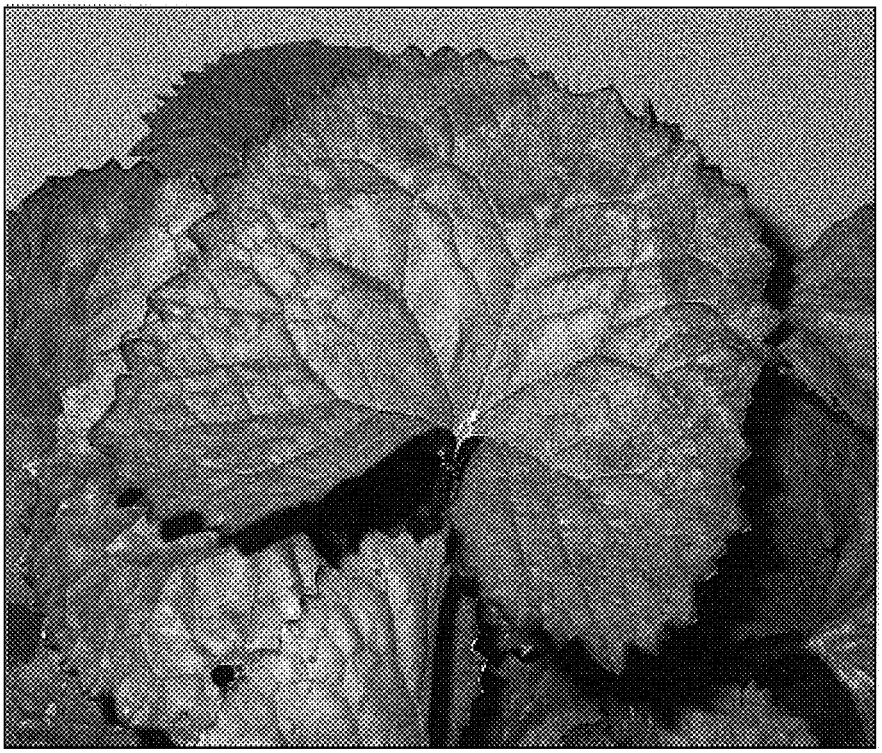

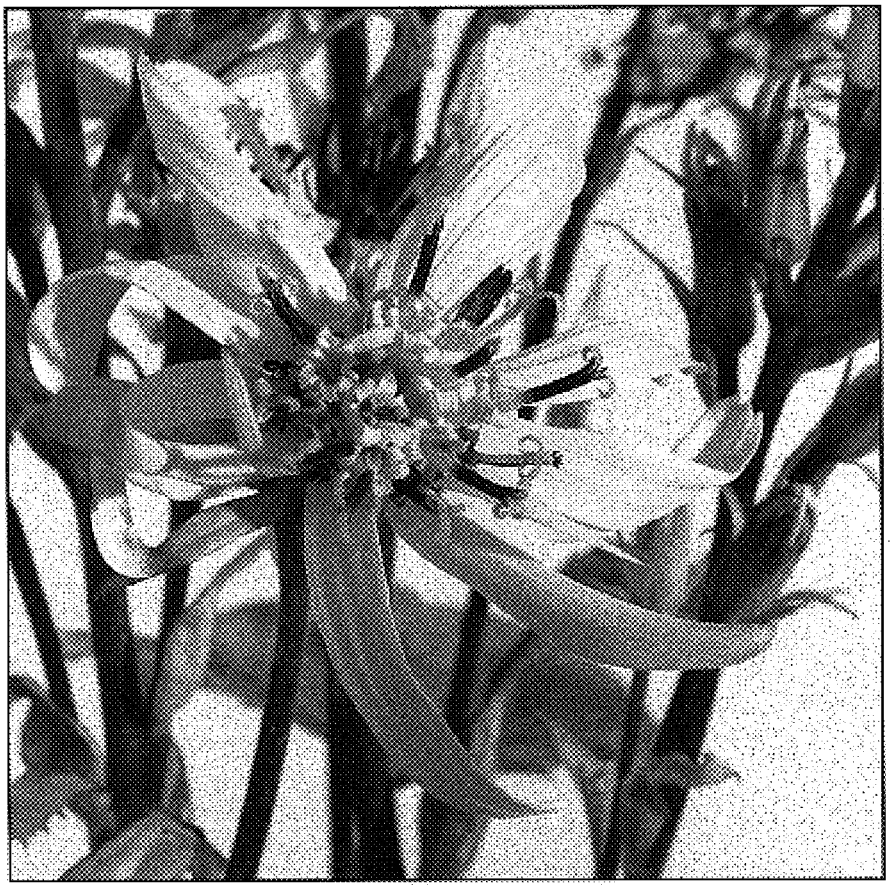
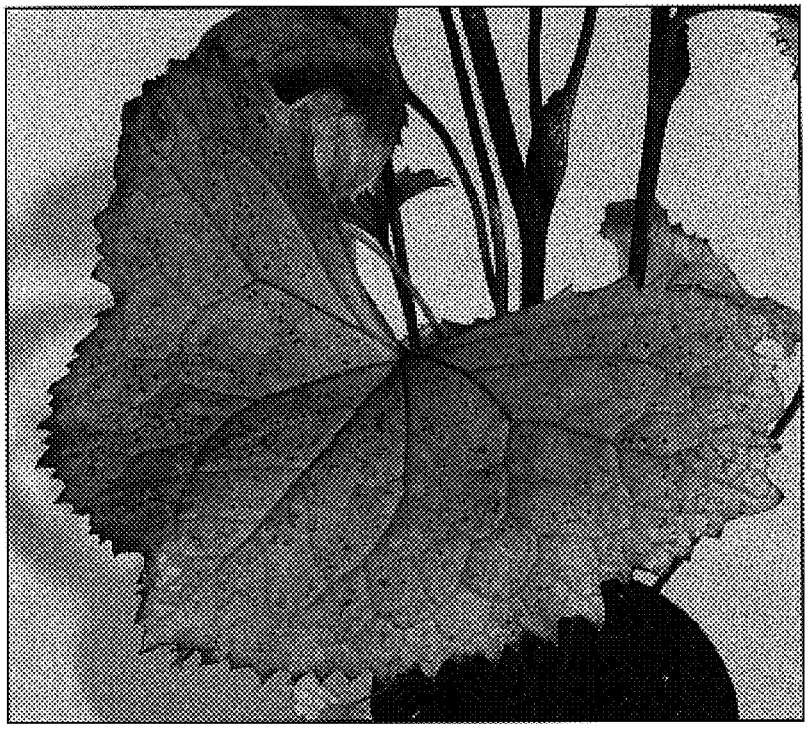

* * * * *